United States Patent [19]
Dilnik et al.

[11] Patent Number: 5,807,367
[45] Date of Patent: Sep. 15, 1998

[54] ABSORBENT ARTICLE HAVING LATERAL BARRIERS

[75] Inventors: Rebecca Lyn Dilnik; Janet Jessie Larsen, both of Neenah, Wis.

[73] Assignee: Kimberly-Clark Worldwide, Inc., Neenah, Wis.

[21] Appl. No.: 757,272

[22] Filed: Nov. 27, 1996

[51] Int. Cl.⁶ .................................................... A61F 13/15
[52] U.S. Cl. ..................... 604/369; 604/385.1; 604/386; 604/387; 604/385.2
[58] Field of Search ................................. 604/365, 366, 604/369, 378, 385.1, 386, 387, 389, 390

[56] References Cited

U.S. PATENT DOCUMENTS

| | | |
|---|---|---|
| 709,223 | 9/1902 | James et al. . |
| 924,337 | 6/1909 | Frommann . |
| 3,346,878 | 10/1967 | Morris .......................................... 2/55 |
| 3,857,394 | 12/1974 | Alemany . |
| 4,072,151 | 2/1978 | Levine . |
| 4,184,498 | 1/1980 | Franco . |
| 4,256,111 | 3/1981 | Lassen . |
| 4,460,364 | 7/1984 | Chen et al. .............................. 604/387 |
| 4,593,053 | 6/1986 | Jevne et al. .............................. 523/111 |
| 4,699,146 | 10/1987 | Sieverding .............................. 128/640 |
| 4,753,648 | 6/1988 | Jackson .................................. 604/389 |
| 4,995,333 | 2/1991 | Keller et al. ............................ 118/300 |
| 5,247,072 | 9/1993 | Ning et al. ................................ 536/97 |
| 5,336,208 | 8/1994 | Rosenbluth et al. ..................... 604/329 |
| 5,618,281 | 4/1997 | Betrabet et al. ......................... 604/387 |

FOREIGN PATENT DOCUMENTS

| | | |
|---|---|---|
| 0 403 692 A1 | 12/1990 | European Pat. Off. . |
| 0 534 488 A1 | 3/1993 | European Pat. Off. . |
| 0 626 158 A1 | 11/1994 | European Pat. Off. . |
| 0 638 303 A1 | 2/1995 | European Pat. Off. . |
| 61-191359 A | 8/1986 | Japan . |
| 5-7222 U | 2/1993 | Japan . |
| 6-9622 U | 2/1994 | Japan . |
| 4-279159 A | 10/1995 | Japan . |
| 2 284 767 | 6/1995 | United Kingdom . |
| WO 93/19711 A1 | 10/1993 | WIPO . |
| WO 95/27459 A1 | 10/1995 | WIPO . |
| WO 96/13238 A1 | 5/1996 | WIPO . |
| WO 96/29968 A1 | 10/1996 | WIPO . |

OTHER PUBLICATIONS

American Society for Testing and Material (ASTM) Designation: D 3574–91, "Standard Test Methods For Flexible Cellular Materials—Slab, Bonded, and Molded Urethane Foams," pp. 164–180, published Mar. 1992.

American Society for Testing and Material (ASTM) Designation: D4440–84, "Standard Practice For Rheological Measurement of Polymer Melts Using Dynamic Mechanical Procedures," pp. 645–648, published Jan. 1985.

Pressure Sensitive Tape Council, PSTC–1, "Peel Adhesion For Single Coated Pressure Sensitive Tapes At 180° Angle," *Test Methods*, tenth edition, copyright 1992, pp. 23–24.

Derwent World Patent Database abstract of WO 95/27459: Description of T. Shimada et al., "Disposable Body fluid Absorbing Article.".

Tse, Mun Fu, "Studies of Triblock Copolymer—Tackifying Resin Interactions By Viscoelasticity and Adhesive Performance," *Journal of Adhesion Science Technology*, vol. 3, No. 7, pp. 551–570 (1989).

Ferry, John D., John Wiley & Sons, "Dependence of Viscoelastic Behavior on Temperature and Pressure," *Viscoelastic Properties of Polymers*, third edition, pp. 264–280, (1980).

*Primary Examiner*—John G. Weiss
*Assistant Examiner*—K. M. Reichle
*Attorney, Agent, or Firm*—Thomas D. Wilhelm; Brian R. Tumm; Mark L. Davis

[57] ABSTRACT

An absorbent article is provided having a central longitudinal axis and barriers positioned on opposing sides of the central axis. The absorbent article further includes an adhesive secured superposed over about 5% to about 100% of the bodyfacing surfaces of the barrier elements. The adhesive has a rheological property tan δ of less than about 0.01 at a frequency of about 0.1 radians per second and a tan δ of less than about 0.1 at a frequency of about 1000 radians per second.

20 Claims, 2 Drawing Sheets

ABSORBENT ARTICLE HAVING LATERAL BARRIERS

BACKGROUND OF THE INVENTION

The present invention relates to articles for absorbing and containing body fluids. Particularly, the invention relates to an absorbent article having lateral barriers with a predetermined amount of adhesive tack which function to occlude fluid migration from the edges of the absorbent article.

All manner and variety of disposable absorbent devices, articles and appliances have been configured for the absorption of body fluids, such as menses, urine, feces and the like are well known. Such disposable absorbent articles are expected to readily absorb any body fluid insulting the body-facing surface thereof, retain the fluid within the absorbent and to prevent the discharged body fluids from soiling the person and/or the adjacent clothing. Examples of such absorbent article include feminine care products, adult incontinence products, training pants and the like.

In the most basic form, the absorbent articles include several common components. Specifically, the disposable absorbent articles include a liquid-permeable, body-facing cover, a liquid-impermeable baffle positioned distally from the cover, and an absorbent material positioned between the cover and the baffle. The absorbent article can also include one or more layers for distributing the body fluid or layers adapted to isolate the cover from the used absorbent to give the cover a dry comfortable feel even when soiled. Typically the absorbent article has one or more means for securing the article during use. Specific types of securement can include adhesives, tapes, belts, side panels, mechanical fasteners and the like.

These absorbent devices, whether utilized as diapers, incontinence garments or sanitary napkins are subject to leakage, and in particular, leakage of liquid from the side edges of the article. Leakage from absorbent devices is generally attributed to a high concentration of fluid absorption at the point of fluid insult. This could be the result of a sudden release of body fluid onto absorbent device, overloading its absorption capability; or the result of a prolonged, steady discharge which may have caused the absorbent material in the device to become super-saturated and unable to accept, to a large degree, additional fluids from the body. Using a sanitary napkin as an illustration, menses will generally migrate radically from the point of insult and will leak from the sides. It has been suggested that at least 20–25 percent of all sanitary napkins experience side leakage. One reason for this is that, when worn, the sanitary napkin can become deformed due to dynamic forces generated as the wearer moves or alters her stationary position. Generally, the sanitary napkin deforms by bunching, twisting, and roping which are all well known in he art. The greatest deformation normally occurs within that part of the article which in use, is located in the narrowest space between the wearer's thighs. As a result of the deformation the surface area of the sanitary napkin is greatly reduced which may lead to the soiling of the wearer's body, typically around the thigh region, and the undergarment.

A wide variety of special components and adaptations have been introduced in disposable absorbent articles in order to reduce or eliminate the incidence of side leakage. For instance, many absorbent articles include elastic structures positioned along the sides of the absorbent material and adjacent at least one of the cover or baffle. The elastic structures are intended to gather at least a portion of the side edge of the absorbent article to form walls, barriers, side seals and the like to impede the flow of liquid past the side edges of the article. In addition to leg elastic structures, absorbent articles have also included elasticized containment flaps which project from the surface of the cover in an attempt to control the movement of liquid and possibly other body wastes toward the side edges of the absorbent article.

A problem associated with barriers, walls and the like is that to prevent liquids from soiling the wearer, the barrier are relatively tall. During use, their size makes them uncomfortable for the wearer and the barrier may fold over and obstruct the absorbent surface. This, in turn, may contribute to the soiling the wearer instead of preventing it.

Improving the performance of a disposable absorbent article continues to be a formidable undertaking, although a umber of improvements have been made in both the materials used and its construction. However, eliminating leakage, particularly along the inside of the thighs without compromising comfort and fit has not yet met the desired needs of the consumer.

Therefore, there remains a need for a sanitary napkin that will be comfortable to wear while decreasing the chance of side leakage associated with the use of sanitary napkins during the menstrual period.

SUMMARY OF THE INVENTION

Briefly, the present invention relates to an absorbent article having longitudinal axis centrally positioned, a body-facing surface and a garment-facing surface. The absorbent article includes a cover disposed toward the body-facing surface, a baffle disposed toward the garment-facing surface and an absorbent positioned between the cover and the baffle. The absorbent article also includes a barrier positioned on either side of the central longitudinal axis for intercepting body fluids migrating toward the side edge of the absorbent article. The absorbent article further includes a pressure sensitive adhesive superposed over at least a portion of the barrier. Adhesives, in accordance with the present invention, have a rheological property, tan delta (tan $\delta$), referenced to about 20° Centigrade of less than bout 0.01 at a frequency of about 0.1 radians per second and a tan $\delta$ of less than about 0.1 at a frequency of about 1000 radians per second. In a preferred embodiment the adhesive has a tan $\delta$ which is below the line A-B. The line A-B is determined by graphically plotting frequency, in radians per second, versus tan $\delta$ at a reference temperature of about 20° C. Point A is a tan $\delta$ of less than about 0.01 at a frequency of about 0.1 radians per second and Point B is a tan $\delta$ of less than about 0.1 at a frequency of about 1000 radians per second.

In a preferred embodiment, he barrier is a foamed adhesive having the above described rheology.

Unexpectedly, it has been discovered that superposing an adhesive of the above qualities over at least a portion of the barrier significantly improves the effectiveness of the barrier in intercepting body fluid when compared to absorbent articles having an adhesive or a barrier alone.

The general object of the present invention is to provide an absorbent article having improved fluid containing properties. A more specific object of the invention is to provide an absorbent article having lateral barrier with an adhesive.

Another object of the invention is to provide a sanitary napkin that is comfortable to wear and which can be readily removed with little or no pain or discomfort to the wearer.

Another object of the invention is to provide a sanitary napkin having good longitudinal liquid distribution and preventing side soiling at the edges of the article.

DETAILED DESCRIPTION OF THE INVENTION

For ease of description, the present invention will be described as being utilized in a preferred embodiment such as catamenial device, i.e., a sanitary napkin. However, one skilled in the art would understand that the invention is not limited thereto and will appreciate the adaptability and utility of the invention in other disposable absorbent structures such as diapers, adult incontinence articles, training pants and the like.

As used herein, the term "sanitary napkin" refers to an article which is worn by females adjacent to the pudendal region and which is intended to absorb and contain various exudates which are discharged from the body, such as, blood, menses and urine. The sanitary napkin is intended to be discarded after a single use. Interlabial devices which reside partially within and partially external of the female wearer's vestibule are also within the scope of this invention. It is to be understood that the invention may be adapted for use in other absorbent particles such as diapers, incontinent devices and the like.

Figure 1:
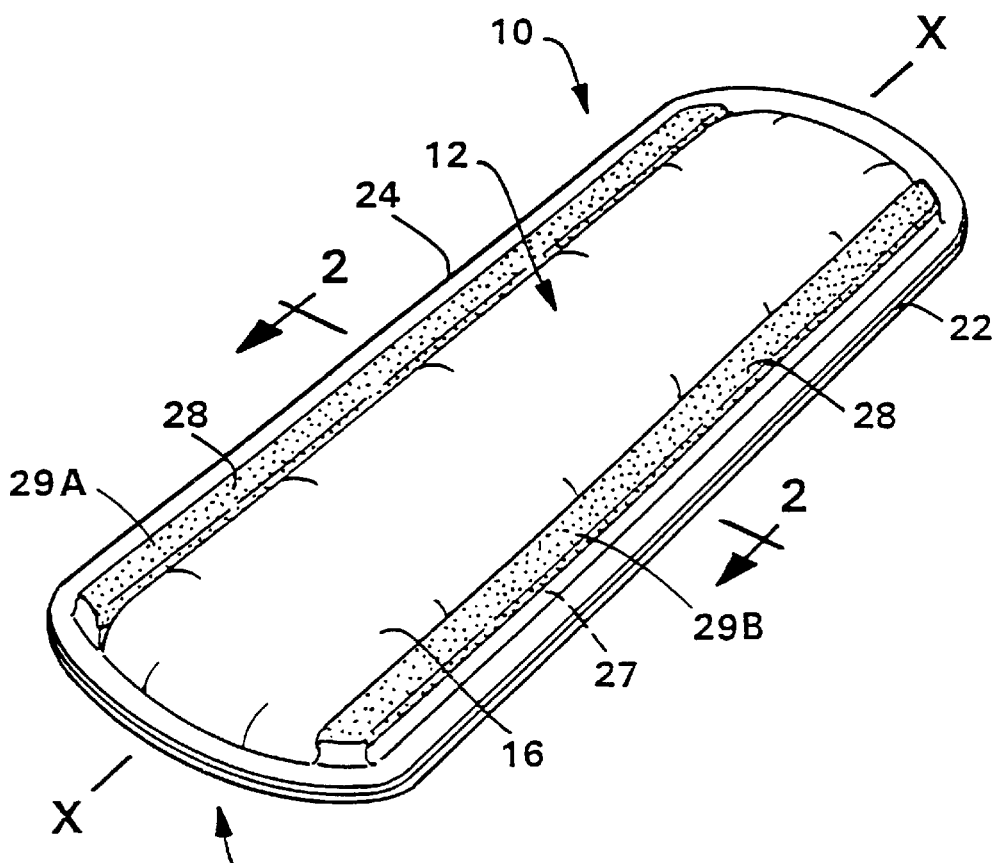
FIG. 1 is a top plan view of an absorbent article showing one embodiment of the invention.
Figure 2:
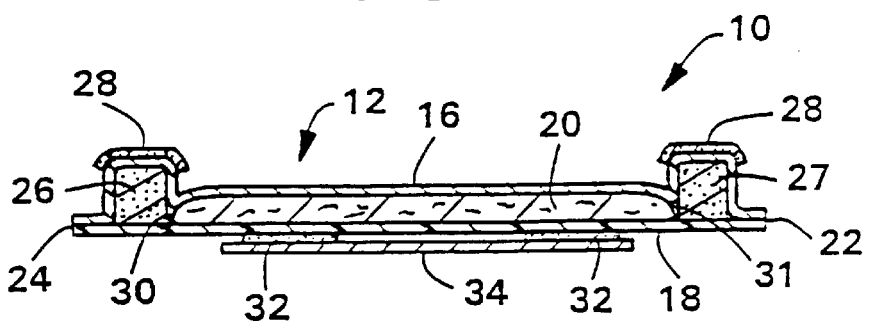
FIG. 2 is a cross-sectional view taken along 2—2 of FIG. 1.

For ease of understanding hen referring to the figures, similar numerals designate like parts in the different views and embodiments. Referring to FIGS. 1 and 2, an embodiment of a sanitary napkin 10 is shown. Although depicted as having generally race track shape, the sanitary napkin 10 can have any variety of shapes well known to those skilled in the art. For example, hourglass, oval etc. The sanitary napkin 10 has a central longitudinal axis X—X, a body-facing surface 12 and a garment-facing surface 14. The term "longitudinal", as used he in, refers to a line, axis or direction in the plane of the sanitary napkin 10 that is generally aligned with or approximately parallel to a vertical plane which bisects a standing wearer into left and right body halves when the sanitary napkin 10 is worn. The body-facing surface 12 is generally understood as that side of the sanitary napkin 10 intended to be directed or positioned adjacent to the body of the wearer while the garment-facing surface 14 is on the opposite side and is intended to reside adjacent to the wearer's undergarments when the sanitary napkin is worn. Accordingly, when referring herein the body-facing surface 12 or the garment-facing surface 14 it is intended to be descriptive of a general orientation, position, or direction of the element or portion of the element.

Generally, the sanitary napkin 10 includes a cover 16, a baffle 18 and an absorbent 20 positioned between the cover 16 and the baffle 18. To prevent body fluids from reaching the sides 22 and 24 of the sanitary napkin 10 barrier structures 26 and 27 are provided. The barrier structure is 26 and 27 are longitudinally positioned between the central longitudinal axis X—X and the sides 22 and 24 of the sanitary napkin 10 and preferably, are positioned parallel to the central longitudinal axis X—X. By providing longitudinal barriers 26 and 27 inward of the sides 22 and 24 the lateral migration of body fluid insulting the body-facing surface 12 can be directed longitudinally along the barriers 26 and 27. Thus, greater utilization of the absorbent 20 is achieved, lessening the likelihood of the sanitary napkin 10 leaking from the sides 22 and 24. The terms "disposed", "disposed on", "disposed near", "disposed at" and variations thereof are intended to mean elemental arrangement such that one element can be integral with another element, or one element can be a separate structure bonded to or placed with or placed adjacent to another element.

The sanitary napkin 10 further includes an adhesive 28 superposed over at least a portion of each barrier structure 26 and 27. Preferably, the adhesive 28 is superposed over at least about 5% of the body-facing surface 12 of each barrier 26 and 27. The adhesive 28 is adapted to secure only a portion of the sanitary napkin 10 to the wearer's body and preferably secures only the barriers 26 and 27 to the wearer.

It has unexpectedly been discovered that the use of an adhesive 28 in conjunction with the barriers 26 and 27 enhances the functionality of each barrier 26 and 27 in preventing liquids from leaking from the sides 22 and 24. The adhesive 28 also enhances the comfort the sanitary napkin 10 during use by retaining the barriers 26 and 27 in a proper relationship relative to the absorbent 20 and the wearer.

Looking at the sanitary napkin 10 in greater detail, the cover 16 is disposed toward the body-facing surface 12 of the sanitary napkin 10 and preferably is adjacent to the absorbent 20. The cover 16, which is designed to contact the wearer's body, is liquid-permeable and should retain little or no fluid in its structure so that it provides a relatively dry surface next to the wearer's skin. The cover 16 can be made from various polymeric films that are apertured to enhance fluid migration into the absorbent 20. The cover 16 can be manufactured from woven or nonwoven fibers or strands produced from natural or synthetic materials which are easily penetrated by body fluids. Thermoplastic polymer films made from polyethylene or polypropylene are preferred. Other acceptable covers might be produced by laminating film and fiber substrates. It can also be beneficial to aperture or emboss (not shown) the cover 16 to increase the rate at which the body fluids can penetrate down and into the absorbent 20.

The cover 16 can have at least a portion of its body-facing surface treated with a surfactant to render the cover 16 more hydrophilic. This results in permitting the insulting liquid to more readily penetrate the cover 16. The surfactant also diminishes the likelihood that the insulting fluid, such as menstrual fluids, will flow off the cover 16 rather than being absorbed by the absorbent 20.

The baffle 18 is liquid-impermeable and is disposed toward the garment-facing surface 14 of the sanitary napkin 10. Preferably, the baffle 18 will permit the passage of air and moisture vapor out of the sanitary napkin 10 while blocking the passage of body fluids. A good material is a micro-embossed, polymeric film, such as polyethylene or polypropylene, having a thickness of about 0.025 to 0.13 millimeters. Bicomponent films can also be used as well as woven and nonwoven fabrics which have been treated to render them liquid-impermeable. Another suitable material is a closed cell polyolefin foam. A closed cell polyethylene foam having a thickness ranging from about 0.5 millimeters to about 10 millimeters works well.

In a preferred embodiment of the sanitary napkin 10, the cover 16 and the baffle 18 extend beyond the absorbent 20 and are bonded together to define the longitudinal sides 22 and 24 of the sanitary napkin 10. The sides 22 and 24 enclose the absorbent 20 to prevent fluid leakage and to form a soft, comfortable side edge for the wearer. The cover 16 and baffle 18 can be bonded together using any means commonly known in the art for this purpose, such as by gluing, crimping, pressure and/or heat-sealing and ultrasonics.

The absorbent 20, which is positioned between the cover 16 and the baffle 18, is generally composed of one or more materials that are hydrophilic, compressible, conformable and non-irritating to the wearer. Acceptable materials are known in the art and include, for example, various natural or synthetic fibers, wood pulp fibers, regenerated cellulose or cotton fibers, or a blend of pulp and other fibers. The absorbent layers may also be comprised of other known materials used in absorbent articles such as cellulose sponge, hydrophilic synthetic sponge, such as polyurethane, and the like. The total absorbent capacity of the absorbent 20 should be compatible with the design exudate loading for the intended use of the sanitary napkin 10.

The absorbent 20 can contain superabsorbent materials which are effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids. Superabsorbents can be incorporated into the absorbent 20 as separate layers or admixed with the cellulose fluff. Superabsorbents may be in the form of flakes, granules, films, particles, fibers or the like.

Barrier structures 26 and 27 are also referred to as first and second barrier elements 26 and 27. The barrier structures 26 and 27 are identical and therefore only one will be described. The barrier 26 is positioned laterally to the central longitudinal axis X—X, between the central longitudinal axis X—X and the side 22 of the sanitary napkin 10. The barrier 26 can reside on top of the cover 16 or desirably, is positioned between the cover 16 and the baffle 18. In a preferred embodiment, the barrier 26 is positioned between the cover 16 and the baffle 18, and adjacent a first longitudinal side edge 30 of the absorbent 20. This arrangement facilitates halting the lateral flow of absorbed liquids toward the side 22 through the absorbent 20 as well as unabsorbed liquids across the cover 16. The barrier 26 may have a linear shape of a line or may be curved while remaining in the area between the central longitudinal axis X—X and the side 22. Desirably, the first barrier 26 is adjacent to the edge 30 following the contour of the absorbent 20. Desirably, second barrier 27 is adjacent second longitudinal side edge 31 and follows the contour of absorbent 20. The barrier 26 extends at least 10% of the absorbent length and preferably, it extends substantially over the full length of the absorbent 20.

As shown in FIG. 1, barrier elements 26 and 27 extend upwardly to first and second top surfaces 29A and 29B. First and second top surfaces 29A and 29B have respective first and second lengths. First and second top sarfaces 29A and 29B are higher than the highest portion of the absorbent and extend at substantially uniform heights along the first and second lengths.

The barrier 26 can be hydrophilic but preferably is hydrophobic. The barrier 26 desirably is constructed of a flexible, easily compressed, resilient material. Suitable materials for forming the barrier 26 include hydrophobic polymer foams, such as, for example, polyurethane foams. Other flexible, resilient materials may be used such as foamed styrene butadiene, foamed polyethylene, foamed silicones, foamed vinyl plastics, soft sponge rubber and the like. Such foams can be obtained from Woodbridge Foam Fabricating, Inc., located at 1120 Judd Road, Chattanooga, Tenn. or from the E. N. Murry Company, Inc., having offices in Denver, Colo.

It is important for comfort and functionality that the barrier 26 be resilient and compressible. The barrier 26 should have a resiliency in the range of about 15% to about 35%, preferably, from about 15% to about 50% and more preferably, from about 15% to about 60%. Resiliency is determined by the ASTM Test Method D3574-91, procedure H.

Compressibility can be in the range of about 0.1 psi to about 2 psi at 50% compression, preferably from about, 0.3 psi to about 1.7 psi and most preferably from about 0.5 psi to about 1.5 psi. Compressibility is determined by the ASTM Test Method D3574-91 procedure C. Desirably, the foamed polymeric material will have a density of about 0.02 grams per cubic centimeter ($cm^3$) to about 0.1 grams per $cm^3$.

The barrier 26 can have a width ranging from about 3 millimeters to about 12 millimeters and preferably the width is from about 3 millimeters to about 8 millimeters. The barrier 26 can have a height ranging from about 2 millimeters to about 25 millimeters; preferably, the height is from about 6 millimeters to about 15 millimeters; and most preferably, the barrier 26 has a height extending above the plane of the absorbent body-facing surface.

The adhesive 28 is superposed over at least a portion of the barrier 26 and preferably is secured to the cover 16 adjacent to the barrier 26. The adhesive 28 can be superposed over approximately 5% to 100% of the barrier 26 body-facing surface. The adhesive 28 can be configured in a substantially regular pattern or an asymmetrical pattern. For example, the adhesive 28 can be dots, ovals, swirls, various linear or non-linear arrays of adhesive longitudinally and/or transversely oriented and reticulated webs having unobstructed interstices between the adhesive fibers or combinations thereof. The adhesive 28 can have a thickness of about 0.01 millimeters to about 2 millimeters. The amount of adhesive 28 applied to the barrier 26 should be enough only to obtain sufficient adherence of the barrier 26 to the wearer to achieve the desired result and provide a satisfactory removal comfort.

The adhesive 28 can be applied to the cover 16 by techniques known in the art. For example, screen printing or extruding the adhesive 28 from one or more nozzles onto the cover 16 as described in the commonly assigned U.S. Pat. No. 4,995,333 issued to Keller et al. on Feb. 26, 1991, the entire disclosure of which is incorporated herein and made a part hereof.

The adhesive 28 deposited in accordance with the present invention may be any pressure sensitive adhesive, and preferably a hot melt adhesive, that is characterized as having specific rheological properties described below. The rheological analysis of an adhesive is a method of determining the viscoelastic property of polymers. Further explanations of polymer rheology and their measurement are discussed in: *Viscoelastic Properties of Polymers*, John D. Ferry, John Wiley & Sons, third edition, pages 264–280 (1980); "Studies of Triblock Copolymer-Tackifying Resin Interactions by Viscoelasticity and Adhesive Performance", Mun Fu Tse, Journal of Adhesion Science Technology, Vol 3. No. 7, pages 551–570 (1989); and test procedure ASTM-D 4440-84 the disclosures of which are incorporated herein by reference and made a part hereof. It is critical to the present invention that the adhesive have a rheology value for tan δ less than about 0.01 at a frequency of about 0.1 radians per second and a tan δ value of less than about 0.1 at a frequency of about 1000 radians per second. It is to be understood that all values for tan δ herein are referenced to 20° Centigrade.

Figure 4:
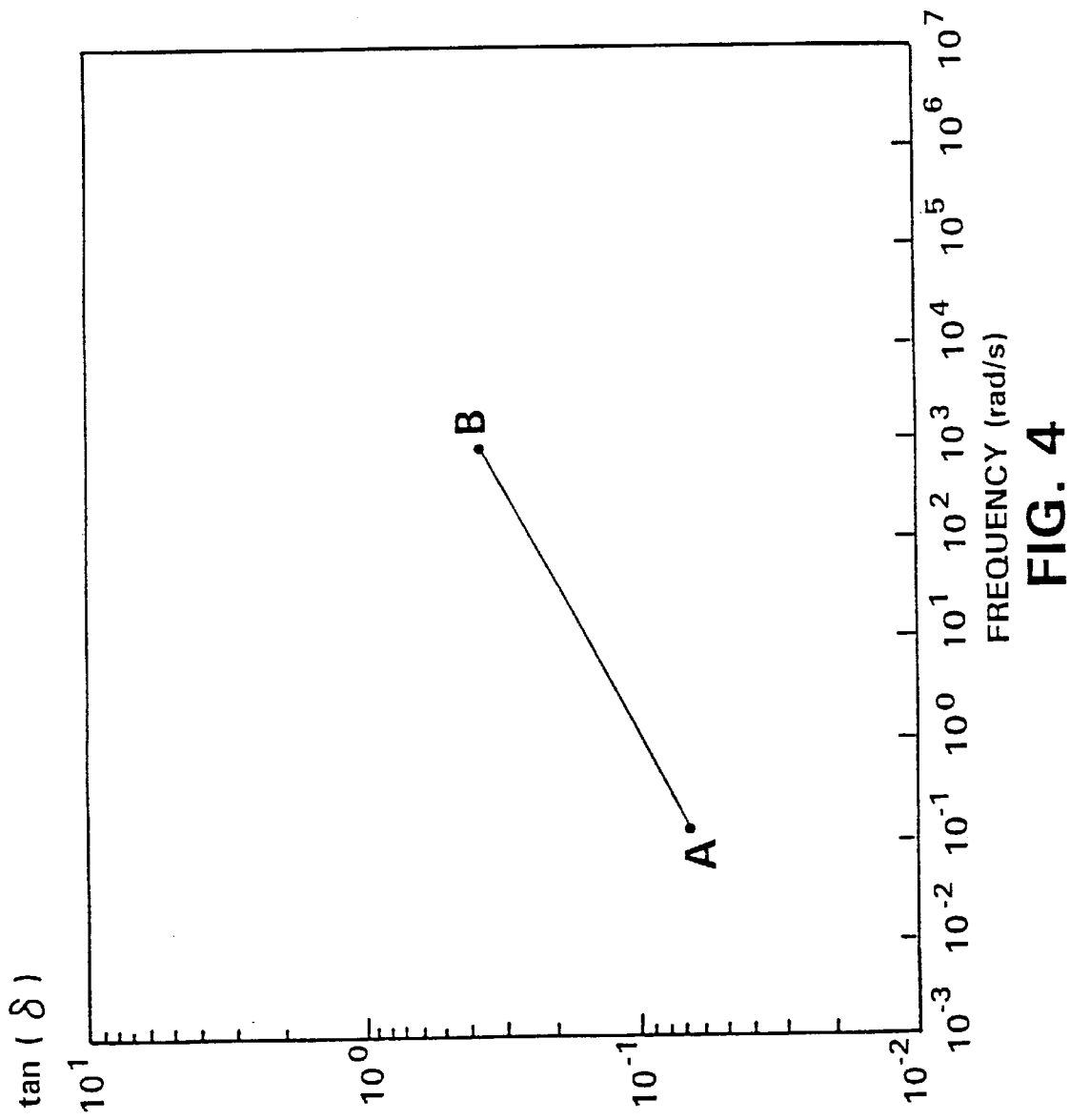
FIG. 4 is a graphical plot of frequency (in radians per second) versus the rheological property tan delta (tan $\delta$) illustrating the line AB.

Referring to FIG. 4, preferred adhesives have a tan δ below the line A-B. Line A-B is determined by graphically plotting, on a log/log scale, frequency versus tan δ where point A is a tan δ of 0.01 at a frequency of about 0.1 radians per second and point B is a tan δ of 0.1 at a frequency of about 1000 radians per second. Adhesives having tan δ values below line AB at frequencies between about 0.1 to about 1000 radians per second lack sufficient adhesion to keep the sanitary napkin 10 securely and comfortably attached to the body of the wearer during use. However, it has been unexpectedly discovered that adhesives having this rheology property will permit the barriers 26 and 27 to remain comfortably secured to the wearer thereby enhancing the gasketing and intercepting characteristics of the barriers 26 and 27.

Suitable adhesives include, for example, Fuller 1419X and Fuller 1430 available from Fuller Adhesive located at 3530 Lexington Ave., St. Paul Minn., 55126-8076.

The rheological quantities for tan δ is measured on bulk adhesive samples not suspended on any substrate and having a thickness of approximately 2 to 3 millimeters. The adhesive is cut into a 25 millimeter diameter circle and placed between two 25 millimeter parallel plate fixtures of the Rheometrics Dynamic Spectrometer, which can be obtained from Rheometrics, Inc. located at 1 PossumTown Road, Piscataway, N.J. 08854. Adhesive samples should be allowed to equilibrate at a selected test temperature before analyzing. A minicomputer governs the application of a 1% peak-to-peak shear strain to the sample. The frequency can be controlled to a fraction of a radian/sec. The values for tan δ are calculated from geometry factors, peak-to-peak amplitude of the torque signal, and phase lag of the torque output wave. Typically, a computer using RHIO testing software available from Rheometrics, Inc., is used to control the operation of the apparatus. Values for time-temperature superposition are calculated between the frequencies of about 0.001 and $10^7$ radians per second using techniques known to those skilled in the adhesive art. Frequency sweeps from 0.1 rad/s to 100 rad/s are run at 10° increments from −60° C. to 120° C. The RHIO testing software shifts the curves relative to a reference temperature of 20° C. From these shifted curves, a "master" curve can be generated.

Figure 3:
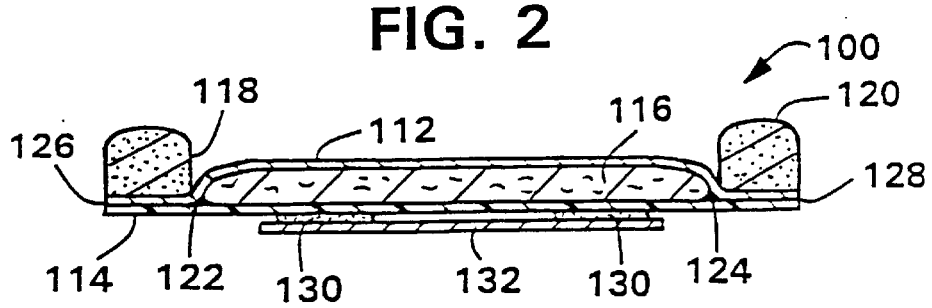
FIG. 3 is a cross-sectional view of another embodiment of the present invention.

Referring to FIG. 3, another embodiment of the invention is illustrated as a sanitary napkin 100. The sanitary napkin 100 has a cover 112, a baffle 114, an absorbent 116 and barrier structures 118 and 120 The cover 112 and baffle 114 extend beyond longitudinal side edges 122 and 124 of the absorbent 116 and are sealed together to form sides 126 and 128 of the sanitary napkin 100. The barrier structures 118 and 120 are secured to the cover 112 between the center longitudinal axis X—X (as seen in FIG. 1) and the sides 126 and 128 of the sanitary napkin 100. Preferably, the barrier structures 118 and 120 are secured to the cover 112 adjacent to the longitudinal side edges 122 and 124.

The barrier structures 118 and 120 are similar to those described above except they are formed by foaming an adhesive to the desired dimensions. Adhesive foaming is generally known and uses apparatus available from Nordson Corporation located at 11475 Lakefield Drive, Duluth, Ga. 30136. Suitable adhesives for foaming include, for example, Findley H5173 and Findley 995-373 which available from Findley Adhesives located at Watertown Plank Road, Wauwatosa Wis., 53226.

Referring to FIGS. 2 and 3, during use the sanitary napkins 10 and 100 can be held in place by any support means or attachment means well-known for such purposes such as a garment adhesive 32 and 130. The garment adhesive 32 and 130 provides a means for securing the sanitary napkin 10 and 100 to the crotch portion of the panty. Thus, a portion or all of the garment facing surface 14 of the backsheet 26 can be coated with the garment adhesive 32 and 130. Any garment adhesive or glue used in the art for such purposes can be used for the garment adhesive herein, with pressure sensitive adhesives being preferred.

The garment adhesive 32 and 130 is typically covered with a removable release liner 34 and 132 in order to keep the adhesive 32 and 130 from drying out or adhering to a surface other than the crotch portion of the panty prior to use. Commercially available release liners commonly used for such purposes can be utilized herein. The sanitary napkin 10 and 100 of the present invention is used by removing the release liner 34 and 132 and thereafter placing the sanitary napkin 10 and 100 in a panty so that the adhesive 32 and 130 contacts the panty. The adhesive 32 and 130 maintains the sanitary napkin 10 and 100 in position within the panty during use. Referring to FIG. 2, when in use the adhesive 28 secured to the cover 16 contacts and lightly adheres to the wearer. Thus, enhancing the performance of the barriers 26 and 27 in deflecting fluids longitudinally along the length of the absorbent 20 and reducing or eliminating the occurrence of side leakage from the sanitary napkin 10.

While the invention has been described with reference to a preferred embodiment and illustrated with regard to a range of optional features, those skilled in the art will appreciate that various substitutions, omissions, changes and modifications may be made without departing from the spirit hereof. Accordingly, it is intended that the foregoing description be deemed merely exemplary of the preferred scope of the present invention and not be deemed a limitation thereof.

We claim:

1. An absorbent article having a central longitudinal axis, and further comprising:
    a) a liquid-permeable cover;
    b) a liquid-impermeable baffle;
    c) an absorbent positioned between said cover and said baffle;
    d) first and second barrier elements for intercepting fluids, said barrier elements being positioned on opposing sides of the central longitudinal axis, said first and second barrier elements facilitating halting lateral flow of liquids; and
    e) adhesive superposed over at least a portion of each of said first and second barrier elements, said adhesive having a rheological property tan δ of less than about 0.01 at a frequency of about 0.1 radians per second and a tan δ of less than about 0.1 at a frequency of about 1000 radians per second.

2. An absorbent article of claim 1 wherein said adhesive is a hot melt adhesive.

3. The absorbent article of claim 1, wherein said adhesive is secured to said cover and superposed over at least about 5% of a body-facing surface of each of said first and second barrier elements.

4. The absorbent article of claim 1, said absorbent further comprising first and second longitudinal side edges, said first and second barrier elements being positioned adjacent respective said first and second longitudinal side edges of said absorbent.

5. The absorbent article of claim 4, said first and second longitudinal side edges having respective first and second lengths, said first and second barrier elements extending at least 10% of the respective lengths of each of said first and second longitudinal side edges.

6. The absorbent article of claim 4, said first and second longitudinal side edges having respective first and second lengths, said first and second barrier elements extending substantially the full respective length of said first and second longitudinal side edges.

7. An absorbent article of claim 1 wherein said adhesive is foamed.

8. The absorbent article of claim 1 wherein said first and second barrier elements are hydrophilic.

9. The absorbent article of claim 8 wherein said first and second barrier elements comprise foam material having a resiliencies of about 15% to about 60%.

10. An absorbent article of claim 9 wherein said foam material has a compressibility of about 0.1 psi to about 2 psi at 50% compression.

11. An absorbent article having a central longitudinal axis, and further comprising:
 a) a liquid-permeable cover;
 b) a liquid-impermeable baffle;
 c) an absorbent positioned between said cover and said baffle;
 d) first and second barrier elements for intercepting fluid, said barrier elements being positioned on opposing sides of the central longitudinal axis, said first and second barrier elements facilitating halting lateral flow of liquids;
 e) adhesive superposed over at least about 5% of said first and second barrier elements, said adhesive having a rheological property tan δ which is below a line A-B between the frequencies of about 0.1 radians per second and about 1000 radians per second, wherein the line A-B is defined by graphically plotting frequency in radians per second versus; tan δ of said adhesive at a reference temperature of about 20° C., the line A-B having as point A a tan δ of less than about 0.01 at a frequency of about 0.1 radians per second and as point B a tan δ of less than about 0.1 at a frequency of about 1000 radians per second.

12. The absorbent article of claim 11 wherein said adhesive is a hot melt adhesive.

13. The absorbent article of claim 11, said absorbent further comprising first and second longitudinal side edges, said first and second barrier elements being positioned between said cover and said baffle, and adjacent respective said first and second longitudinal side edges of said absorbent.

14. The absorbent article of claim 13, said longitudinal side edges having respective first and second lengths, said first and second barrier elements extending substantially the full respective length of said first and second longitudinal side edges.

15. The absorbent article of claim 11 wherein said adhesive is superposed over about 5% to 100% of a body facing surface of each of said first and second barrier elements.

16. A sanitary napkin having a central longitudinal axis, and further comprising:
 a) a liquid-permeable cover;
 b) a liquid-impermeable baffle;
 c) an absorbent positioned between said cover and said baffle;
 d) first and second harrier elements for intercepting fluid, said barrier element being secured to said cover on opposing sides of the central longitudinal axis, said first and second barrier elements comprising a hot melt adhesive having a rheological property tan δ which is below a line A-B, wherein the line A-B is defined by graphically plotting frequency in radians per second versus tan δ of said adhesive at a reference temperature of about 20° C., the line A-B having as point A a tan δ of less than about 0.01 at a frequency of about 0.1 radians per second and as point B a tan δ of less than about 0.1 at a frequency of about 1000 radians per second.

17. The sanitary napkin of claim 16 wherein said absorbent has first and second longitudinal side edges and wherein said first and second barrier elements are positioned adjacent respective said first and second longitudinal side edges.

18. The sanitary napkin of claim 17, said first and second longitudinal side edges having respective first and second lengths, said first and second barrier elements extending substantially the full respective length of said first and second longitudinal side edges.

19. The sanitary napkin of claim 16 wherein said adhesive is foamed.

20. The sanitary napkin of claim 16 wherein said first and second barrier elements have respective first and second heights, the first and second heights extending above a plane of a top surface of said absorbent.

* * * * *